United States Patent
Wilson et al.

(10) Patent No.: US 6,859,517 B2
(45) Date of Patent: Feb. 22, 2005

(54) DUAL X-RAY FLUORESCENCE SPECTROMETER AND METHOD FOR FLUID ANALYSIS

(75) Inventors: Bary W. Wilson, Ft. Lauderdale, FL (US); Chester L. Shepard, W. Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 80 days.

(21) Appl. No.: 10/420,460

(22) Filed: Apr. 22, 2003

(65) Prior Publication Data

US 2004/0213373 A1 Oct. 28, 2004

(51) Int. Cl.[7] .............................................. G01N 23/223
(52) U.S. Cl. .............................. 378/47; 378/44; 378/45
(58) Field of Search ................................. 378/42, 44–50

(56) References Cited

U.S. PATENT DOCUMENTS

| | | |
|---|---|---|
| 3,751,661 A | 8/1973 | Packer et al. |
| 4,125,769 A | 11/1978 | Marten et al. |
| 4,228,353 A | 10/1980 | Johnson |
| 4,388,530 A | 6/1983 | Lubecki et al. |
| 4,567,012 A | 1/1986 | Radcliff |
| 4,683,759 A | 8/1987 | Skarsvaag et al. |
| 4,720,842 A | 1/1988 | Kira et al. |
| 4,795,903 A | 1/1989 | Clayton |
| 4,959,848 A | 9/1990 | Parobek |
| 5,497,008 A | 3/1996 | Kumakhov |
| 5,598,451 A | 1/1997 | Ohno et al. |
| 5,657,363 A | 8/1997 | Hossain et al. |
| 5,712,891 A * | 1/1998 | Benony et al. ................ 378/47 |
| 5,721,759 A | 2/1998 | Raatikainen |
| 5,742,660 A | 4/1998 | Majewski et al. |
| 5,982,847 A * | 11/1999 | Nelson ......................... 378/47 |
| 6,009,760 A | 1/2000 | Jakkula et al. |
| 6,012,325 A | 1/2000 | Ma |
| 6,031,565 A | 2/2000 | Getty et al. |
| 6,226,347 B1 | 5/2001 | Golenhofen |
| 6,285,734 B1 | 9/2001 | von Alfthan |
| 6,408,048 B2 | 6/2002 | Opsal et al. |

* cited by examiner

*Primary Examiner*—Edward J. Glick
*Assistant Examiner*—Hoon Song
(74) *Attorney, Agent, or Firm*—Woodard, Emhardt, Moriarty, McNett & Henry LLP

(57) ABSTRACT

Disclosed are an X-ray fluorescence (SRF) spectrometer and method for on-site and in-line determination of contaminant elements in lubricating oils and in fuel oils on board a marine vessel. An XRF source block 13 contains two radionuclide sources 16, 17 (e.g. Cd 109 and Fe 55), each oriented 180 degrees from the other to excite separate targets. The Cd 109 source 16 excites sample lube oil flowing through a low molecular weight sample line 18. The Fe 55 source 17 excites fuel oil manually presented to the source beam inside a low molecular weight vial 26 or other container. Two separate detectors A and B are arranged to detect the fluorescent x-rays from the targets, photons from the analyte atoms in the lube oil for example, and sulfur identifying x-rays from bunker fuel oil for example. The system allows both automated in-line and manual on-site analysis using one set of signal processing and multi-channel analyzer electronics 34, 37 as well as one computer 39 and user interface 43.

44 Claims, 3 Drawing Sheets

DUAL X-RAY FLUORESCENCE SPECTROMETER AND METHOD FOR FLUID ANALYSIS

RELATED APPLICATION DATA

This application is related to application Ser. No. 10/041,331 filed Jan. 7, 2003, and to application Ser. No. 09/776,109 filed Feb. 1,2001, and to application Ser. No. 09/447,036 filed Nov. 19, 1999.

GOVERNMENT RIGHTS

This invention was made with Government support under Contract Number DE-AC0676RL01830 awarded by the U.S. Department of Energy. The Government has certain rights in the invention.

FIELD OF THE INVENTION

The present invention relates to an apparatus and method for fluid analysis. Particular embodiments of the present invention relate to systems and techniques for x-ray fluorescence analysis of fluids. Still more particular embodiments are related to on-board x-ray analysis of operating machine fluids and fuels for the determination of machine health and fuel condition.

BACKGROUND

It is well known that chemical and physical analysis of a machine fluid can provide information about the condition of the fluid as well as the wear status of the machine in which the fluid is used. Machine fluid analysis is widely used for determination of lubricant condition, lubricant contamination and wear status in engines, drive components and hydraulic systems in fleet or industrial service. For example, lubrication oil analysis is widely used for railroad engines and is conducted by the military on most motorized equipment including aircraft and naval engines and lubricated drive components. In industry, commercial fluid analysis providers offer fluid analysis service for engine and drive train lubricants as well as hydraulic fluids.

However, traditionally, an oil sample has been taken from the lubricant reservoir on the engine being analyzed, with fluid parameters then measured in the laboratory. To avoid inefficiencies and difficulties associated with such batch analysis, it is desirable to develop systems and devices capable of operation on board a machine to provide continuous and real time monitoring of machine fluids.

One type of fluid analysis, x-ray fluorescence analysis, has the potential to be used to quantify trace amounts of materials in machine fluids, provided the x-ray fluorescence meter employed is sufficiently sensitive to the material to be detected. However, for a variety of reasons, many x-ray fluorescence meter designs are not readily applicable for on-board machine fluid analysis.

For example, while not as important for most laboratory scale spectrometer applications, for an on-board machine fluid application, it is advantageous to have a compact spectrometer. However, the sensitivity of a spectrometer is typically compromised by attempts to limit its size because, as the device becomes smaller, components necessarily get closer together, increasing the relative significance of noise. In addition, a smaller device may be more susceptible to breaking or failure from the potentially harsh environment on-board a machine. As a final example, in order to be feasible for dedicated application to individual machines, an x-ray fluorescence meter must be economical to manufacture.

Therefore, a need exists for an x-ray fluorescence spectrometer that is both compact and sensitive so as to be useful in on-board machine fluid analysis. A need also exists for an x-ray fluorescence spectrometer that is capable of meeting the rigors of on-board application yet is economical and efficient to construct. The invention described in the above-mentioned application Ser. No. 10/1041,331 filed Jan. 7, 2003 addresses one or more of these or other needs.

In addition to lubricants and hydraulic fluids in machines, certain machines requiring fuel are totally dependent on the condition of fuel supplied to achieve optimum performance. This is particularly true in the marine propulsion maintenance industry, wherein both lube oil analysis and bunker fuel analysis are important for proper maintenance and operation of a ship. In this industry, and in others as well, there is value in having the ability to simultaneous perform analysis of different samples. It is also advantageous to have multi-analysis capabilities where one analysis is automated ongoing in-line analysis, and another provides on-board manual analysis of fuels and lubricants. At the same time, there remains the need for apparatus that is reasonably sturdy, accurate, reliable, inexpensive and compact. The present invention is addressed to one or more of these needs.

SUMMARY

The invention is set forth in the claims below, and the following is not in any way to limit, define, or otherwise establish the scope of legal protection. In general terms, the present invention relates to x-ray fluorescence analysis of fluids.

One aspect of the invention is providing an x-ray fluorescence spectrometer having a single source block containing two x-ray sources, with the source block accommodating two separate fluid samples for performing different x-ray fluorescence analysis on each sample. Another aspect of the invention is accommodation in the source block of two different fluids, one for excitation by the one x-ray source and the other for excitation by the other x-ray source, wherein the x-ray sources can each be selected to provide x-rays in th cenergy range of interest for the respective fluid. Another aspect is providing for one of the fluids to be flowing and the other to be in a sample batch. Another aspect is having individual x-ray detectors, one for the fluorescence response from the one fluid, and the other for the fluorescence response from the other fluid, and coupling the detectors to a shared analyzer. Another aspect is the use of a multi-channel analyzer under computer control. Another aspect is the use of such spectrometer in combination with a system using the flowing fluid and supplied by the other fluid from which the batched samples are taken. Another aspect of the invention is the use in the system of an internal combustion engine wherein the flowing fluid is lubricating oil and wherein the second fluid is engine fuel oil.

Other aspects of the invention will be recognized from the specification and claims following herein.

BRIEF DESCRIPTION THE DRAWINGS

DESCRIPTION OF THE ILLUSTRATED EMBODIMENT

Figure 1:
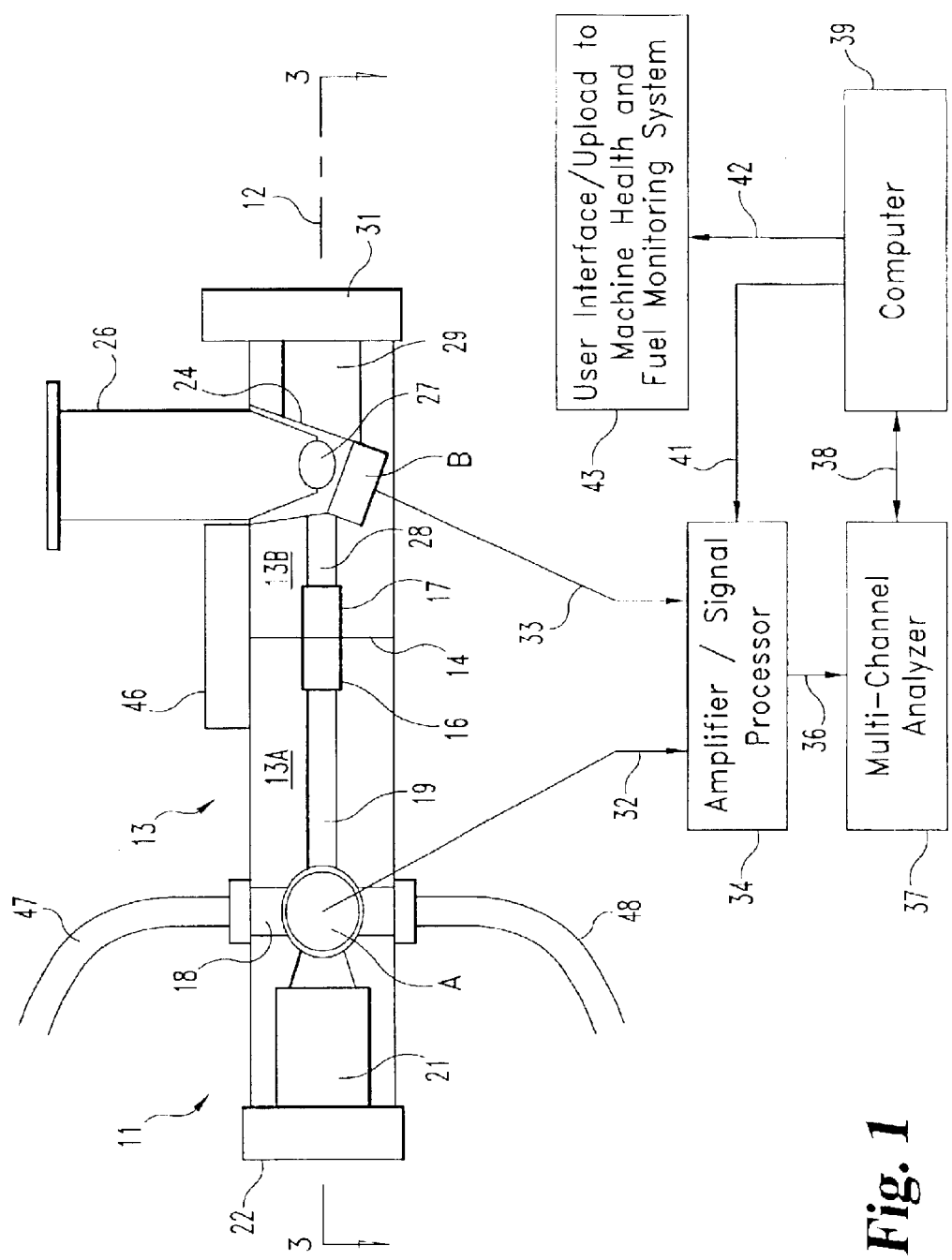
FIG. 1 is schematic diagram of an x-ray fluorescence meter according to a typical embodiment of the invention.

For the purposes of promoting an understanding of the principles of the invention reference will now be made to the embodiments illustrated in the drawings and specific language will be used to describe the same where like reference numerals are used to describe like structures. It will nevertheless be understood that no limitation of the scope of the invention is thereby intended. Any alterations and further modifications in the illustrated embodiments, and any further applications of the principles of the invention as illustrated herein being contemplated as would normally occur to one skilled in the art to which the invention relates.

Figure 3:
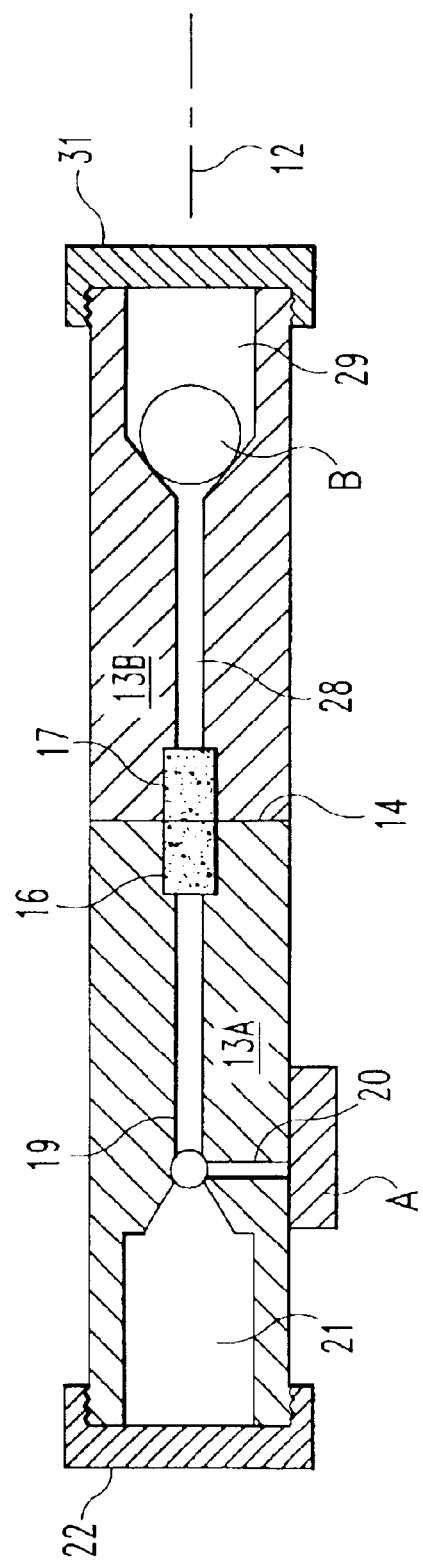
FIG. 3 is a sectional view of the housing of the FIG. 1 x-ray fuorescence meter.

Referring now to FIGS. 1 and 3 of the drawings, a housing 11 which is generally cylindrical about a longitudinal axis 12, encloses a source block assembly 13 having a partition 14 establishing a sampling portion 13A for flowing engine lubricating oil and sampling portion 13B for a batch sample of fuel oil from a fuel bunker. An isotopic source 16 of x-rays is provided in source block portion 13A adjacent partition 14. Similarly, a source 17 of x-rays is provided in source block portion 13B. A transverse passageway 18 is provided in source block portion 13A and intersects a radiation passageway 19 from the source 16 to a noise reduction cavity 21 near the left-end of the assembly and which is closed by the end block shield 22. Similarly, a sample insertion and receiver well 24 is located in the source block portion 13B and enables reception therein of a fuel oil sample vial 26. The fuel oil sample 27 at the lower end of the vial intercepts a radiation passageway 28 from the radiation source 17 to the noise reduction cavity 29 which is closed at the right-hand end of the assembly by the end block shield 31. According to one aspect of the invention shown in the illustrated embodiment, the primary radiation passageways 19 and 28 are shown in-line on a common axis 12 in a single source block with partitioning at 14 and with radionuclide sources 16 and 17, each oriented 180 degrees to the other. But it should be understood that some other aspects of the invention can be implemented also with the primary radiation passageways from the sources to the targets oriented otherwise than in-line. For example, in one aspect, the primary radiation passageways are oriented at an angle greater than 90 degrees, for example within about 30 degrees of 180 degree alignment. In other aspects, the primary radiation passageways are oriented at an arbitrary angle as dictated by design consideration such as compactness or geometric constraints or user accessibility or serviceability.

A silicon PIN diode detector A is seated at the end of a short stub passageway 20 (see FIG. 3) transverse to both passageway 18 for the flowing oil, and also to passageway 19 for the radiation from the source 16 toward the noise reduction chamber 21. A second Si PIN detector B is located immediately adjacent the bottom of the batch sample insertion well and is thereby adjacent the fuel oil sample at the lower end of the sample vial. Each of these radiation detectors has output signal lines such as line 32 for detector A and 33 for detector B. These are coupled to an amplifier/signal processor 34 having such amplification of input and output signals as may be needed. The output at 36 is to a multi-channel analyzer 37. The analyzer communicates both ways with computer 39, as symbolized by line 38. The computer also has a feedback output at 41 to the processor 34 and an output at 42 to a user interface/upload device 43.

Such devices as the amplifier/signal processor 34, multi-channel analyzer 37, computer 39 and interface 43 are well known in the art and commercially available. For instance, the model PX2T power supply and amplifier manufactured by Amptek would serve for the amplifier/signal processor and the model MCA8000A also manufactured by Amptek would serve as the multi-channel analyzer. Any of a host of PC-based computers manufactured by Dell, Gateway, Hewlett Packard, and others are available. Interface computer boards such as those made by National Instruments are also available. The amplification and signal processing in the processor 34 is controlled by computer 39 through coupling 41 on a time sharing basis to enable the analyzer 37 to periodically analyze the oil flowing through the passageway 18.

Depending upon the needs of the user, the user interface may be a data recorder, a viewing screen, a filter control, a fuel valve, an alarm system, a machine shut-down system, or any of a variety of devices.

Because of the fact that it is not likely that there would be continuous batch sampling, a slide-back shutter 46 of radiation shielding material is provided on the device to close the sample insertion well when batch sampling is not being done.

The x-ray sources can be any conventional source of x-rays. In one form the x-ray sources are selected to provide excitation x-rays in the energy bands of interest for the elements to be detected in the fluid. For contaminant elements normally of concern in lubricating oil for machinery, a likely radiation source 16 of x-rays may be cadmium 109. For contaminants of concern in connection with bunker fuel, for example, a radiation source 17 of x-rays may be iron 55. The source block 13 is constructed of a material that provides suitable shielding to surrounding people and structures, and in one form is selected to not significantly contribute to noise through interaction with the source x-rays. Selection of the material for source block will depend on the energy of the source x-rays and the elements of analytical interest and include consisting of low atomic number elements such as carbon. Portions 13A and 13B can be constructed of the same or different material. For example, sampling portions 13A may be aluminum and lead with portion 13B constructed of plastic, such as DELRIN™ or ULTEM™.

One way to move the flowing oil through block portion 13A is to use an x-ray transparent tube in passageway 18 connected to the in-flow line 47 and outflow line 48 in the same manner as described in the above-mentioned application Ser. No. 10/041,331. Suitable tubes can be thin walled and constructed of materials of low atomic weight, for example substantially below the atomic weight of the elements that are to be detected in the fluid. For example the tube may be polyimide. Similarly, shielding materials and techniques as used in the 10/041,331 application can be used in the practice of the present invention. Therefore, the disclosure of that application and the other two applications mentioned herein are incorporated in their entirety herein by reference. If the installation site and nature of the vehicle or vessel will accommodate greater volume and weight of the meter assembly, common shielding materials and techniques may be used instead of the inventive ones disclosed in above-mentioned application Ser. No. 10/041,331.

The purpose of the noise reduction chambers 21 and 29 are to receive the direct radiation from the sources 16 and 17 to reduce the noise at detectors A and B attributable to interaction of the excitation radiation with the source block material. The chambers 21 and 29 can be sized to provide substantial separation and distance between the walls of the chambers 21 and 29 and the detectors A and B. For example, in the illustrated embodiment, the dimension of the chambers 21 and 29 relative to the line between the respective source and fluid targets (axis 12) can be substantially greater than the size dimension of the passageways 19 and 28 relative to this line, for example at least 2 times greater or 3 or 5 times greater. In other aspects, for example where other shielding techniques are utilized or where noise attributable to interactions of the source x-rays and the source block walls are not of concern, the chambers 21 and 29 can be smaller or eliminated.

Figure 2:
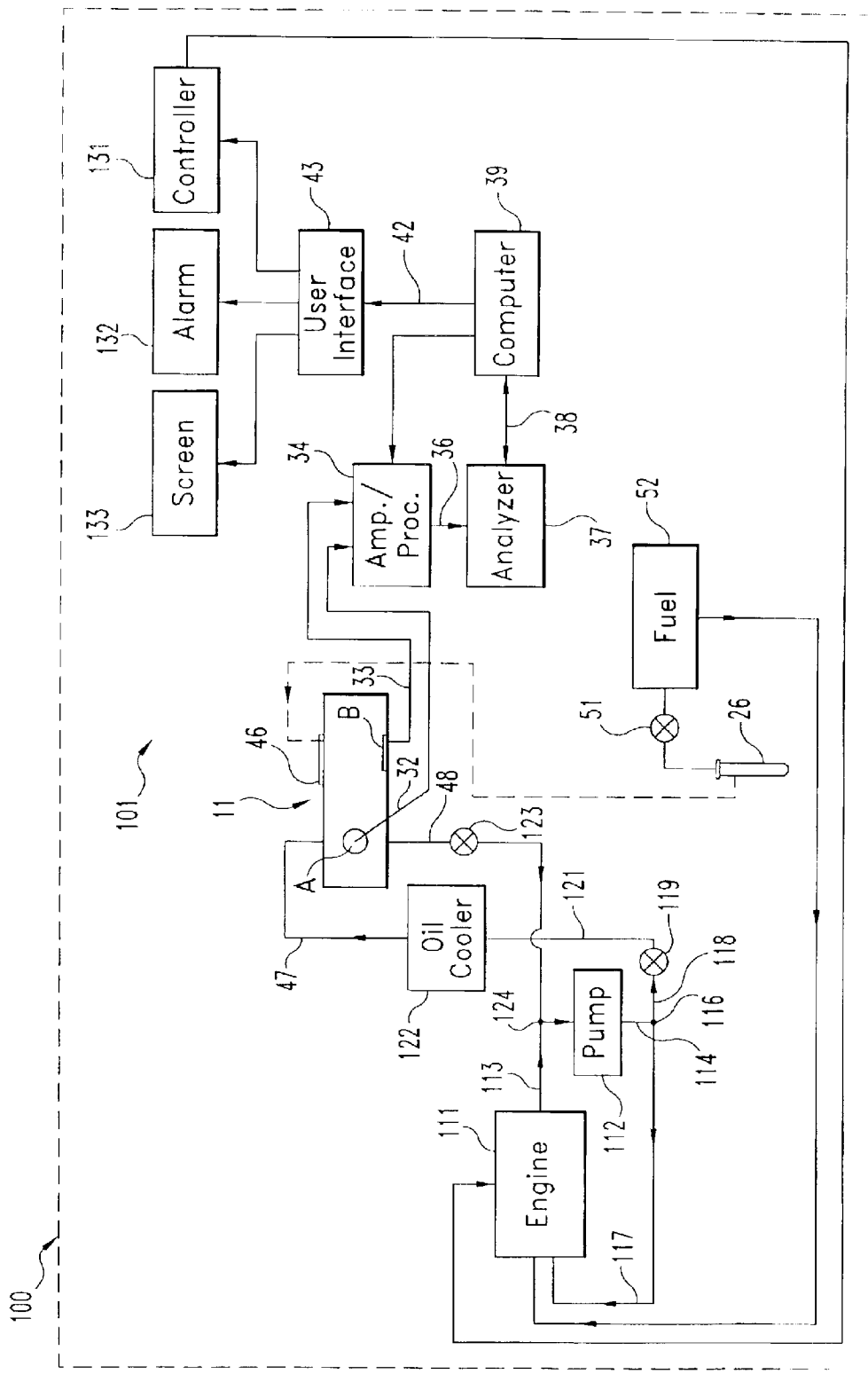
FIG. 2 is a schematic illustration of a boat with portions of a marine propulsion system utilizing an x-ray fluorescence meter of the FIG. 1 embodiment of the present invention in a system on board the boat for real time sampling of flowing lubricating oil and batch sampling of bunker fuel oil according to a further embodiment of the present invention.

Turning now to FIG. 2, boat depicted as block 100, has on board, a system 101 for monitoring lubricating oil from an engine and fuel oil from bunker storage. The engine 111 has a lubricating oil pump 112 with a pump intake line 113 and discharge line 114. The discharge line has a tee junction at 116 to split the flow for supplying the engine on line 117 and supplying oil for sampling on line 118 to master valve 119. When valve 119 is open, a portion of the oil flowing in line 114 passes through valve 119, line 121 and oil cooler 122 into the oil sample line 47 of the housing 11 of the x-ray fluorescence meter of FIG. 1. Oil exiting housing 11 on line 48 then passes through a one-way valve 123 before re-joining oil flow from the engine to the pump inlet at tee junction 124.

The signal processor with amplifier 34 is capable of receiving and amplifying signals from both detector A for the flowing oil and from detector B for a fuel oil sample in a vial in the receiver well 24. Device 34 is controlled by computer 39 for automatic periodic sampling and outputting signals representative of radiation fluorescence from oil flowing in sample line 47, or continuous sampling of the flowing oil, but switching when and as needed for analysis of a fuel oil sample in a vial in well 24.

Computer 39, receiving signals from the analyzer and from any desired manual inputs, includes signal processing electronics and programming instructions operable to determine the presence and the amount of wear metal particles or other contaminants of interest in the lubricating oil in line 47 based on the signals received from the x-ray detector A, and the presence and amount of fuel oil constituents of interest from the bunker/s 52. The computer 39 can be any of many general purpose computers commercially available and programmed to cooperate with the analyzer 37 to perform the tasks normally related to x-ray fluorescence spectroscopy according to the present invention. Alternatively, special purpose computers designed specifically to accomplish one or more of the simple tasks to implement the present invention, can also be used. Tasks to be performed include collecting fluorescent x-ray intensity data, subtracting background data, and converting fluorescent x-ray data into part per million concentration values. The computer and accompanying programs are one embodiment of a structure capable of processing the signals from the x-ray fluorescence sampler in order to determine the presence and amount of wear metal particles in the lubricating oil in the engine, and presence and amount of contaminants or constituents of interest in fuel oil. Alternatively, or in addition, multi-channel detectors may be used at A and/or B to quantitatively determine fluorescent photon counts for photons having different energy levels. Computer 39, operating with such detectors and programming instructions operable to fit signature fluorescence spectra from known elements, can thereby determine the presence of multiple elements in a single sample.

The manual insertion mode for a batch-type sample in a vial is represented in FIG.2 by the vial 26 associated with valve 51 on fuel bunker 52. After taking a sample from the fuel bunker, the slide 46 on the sampler is opened and the vial is inserted. In response to a switch in the sample receiver well 24 (FIG. 1) or a manually operated key or the like which is on a computer keyboard or otherwise coupled to the computer 39, the computer controls the processor 34 to transmit signals responsive to detector B for analysis and output results to the computer for reporting to the interface 43. The fuel sample can then be removed from the sampler and discarded or returned to the bunker. The apparatus can serve as many bunkers as desired and as frequently as desired.

As mentioned above, sampling and analyzing of flowing fluid such as lubricating oil, for example, can be automatically done continuously. Batch sampling as in the vial 26, if manually done rather than by robot, for example, will be done periodically. Therefore, as mentioned above, the sampling and analyzing of a batch may take priority over a continuous sampling of flowing fluid. In such case, the sampling and analysis of the flowing fluid may be interrupted by an operator manually pressing a key or using voice activation, or automatically when a vial is inserted in the sampler or by any other means desired. Following the batch sampling event, the automatic continuous or periodic sampling of flowing oil may resume.

Another approach is simultaneous sampling and analysis of a flowing oil sample and bunker fuel sample by using the multi-channel analyzer. Signals received from the detectors A and B are separated in the processor 34 and separately transmitted to the multi-channel analyzer for separate analysis and transmission of results to computer 39 for storage and for transmission to the user interface and then to a controller 131, for example, or to an alarm or annunciator 132, or to a viewing screen 133. Other receivers of the computer output may also be used. An output signal line 136 is shown from computer 131 to the engine 111. The signal on such line could be used to control speed or load or to shut-down an engine in response to detection of excessive metal in the lubricating oil, indicating impending failure of the engine due to excessive wear or destruction of one or more engine components. Other outputs from the computer can be used to do any of a variety of things. Some examples are to trigger an alarm such as at 132 or to generate a screen display at 133 or a paper chart showing contamination or deterioration of lubricant during a period of time. A computer can do any or all of these and other things. Thus it is seen that, as another example, computer 39 also outputs through suitable interfacing at 43, the determined concentration data to a system operator or controller 131. As one example, the concentration values can be transmitted wirelessly to a remote observer of engine health in the manner described in U.S. application Ser. No. 09/776,109 filed Feb. 1, 2001, and assigned to the same assignee of the present invention.

In the illustrated embodiment, the flowing oil sampler is connected to oil line 116 separately from the main oil line 117, and thus interrogates oil selectively diverted from the main line. It is also contemplated that the sampler can be provided in oil line 114, 117 and thus be operable to interrogate all engine oil from pump 112 rather than a portion oil selectively diverted therefrom.

It is understood that while the primary focus of the description above relates to engine oil and fuel, the present invention should not be so limited. As may be apparent to those skilled in the art after reading this specification, such an x-ray fluorescence apparatus and method have applications to fluids while flowing, and to fluids in storage. As one example, the techniques described herein would be useful to analyze concentrations of constituents in a fluid process line at an industrial facility. A particular example would be to measure suspended metals or soaps in fluids flowing in a process line, and sampling fluids from tanks of fluids received from vendors, before admitting such fluids to the process lines.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the invention described herein are desired to be protected. For example, in the claims which follow, where the term "input" or "output" is used in connection with reference to an electronic device, it should be understood to comprehend singular or plural and one or more signal channels as appropriate in the context. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. All publications, patents, and patent applications cited in this specification are herein incorporated by reference as if each were specifically and individually indicated to be incorporated by reference and set forth in its entirety herein.

What is claimed is:

1. An x-ray fluorescence spectrometer for on-site determination of presence of some elements in flowing fluids and some elements in batch samples of fluids comprising:
   a sampler body having a first passageway therein for passage of flowing fluid through the body, and
   said sampler body having a receiver therein for receiving a batch sample of a fluid;
   a first x-ray radiation source located in said body;
   a second x-ray radiation source located in said body;
   a second passageway located in said body and communicating between said first x-ray source and said first passageway;
   a third passageway located in said body and communicating between said second x-ray source and said batch sample receiver;
   a first radiation detector coupled to said body and having a signal output means;
   a fourth passageway located in said body and communicating between said first passageway and said first radiation detector;
   a second radiation detector coupled to said body and having signal output means;
   a fifth radiation response passageway located in said body and communicating between said batch receiver and said second radiation detector;
   a signal processor having inputs coupled to said output means and receiving signals from said detectors, and having output means;
   an analyzer having an input coupled to said signal processor output means and operable to analyze signals from said processor and produce output signals representing certain chemical components of said flowing fluid and certain chemical components of said fluid batch samples; and
   a computer having an input coupled to said analyzer and an output to at least one interface for using the results of analysis by said analyzer of said signals from said processor.

2. The spectrometer of claim 1 wherein:
said first and second passageways are in a portion of said body made of material forming a shield to radiation from said first x-ray source except through said second passageway to said first passageway;
said third passageway and said receiver are in a portion of said body made of material forming a shield to radiation from said second x-ray source except through said third passageway to said receiver.

3. The spectrometer of claim 2 wherein:
said second and third passageways have colinear axes;
said first source is at an end of said second passageway;
said second source is at an end of said third passageway and is proximate said first source.

4. The spectrometer of claim 3 wherein:
said fourth passageway is located in a portion of said body made of material forming a shield to radiation from fluid flowing in said first passageway and excited by radiation from said first source; and
said fifth passageway is located in a portion of said body made of material forming a shield to radiation from a sample fluid in said receiver and excited by radiation from said second source.

5. The spectrometer of claim 4 wherein:
at least a portion of said body material is selected from the group consisting of tungsten, lead, aluminum, and plastic.

6. The spectrometer of claim 4 wherein;
said first source is cadmium 109 and said second source is iron 55.

7. The spectrometer of claim 3 wherein:
the body material in which said first passageway is located is different than the body material in which said second passageway is located.

8. The spectrometer of claim 1 wherein:
said computer also has output coupled to said analyzer to control sampling and processing events for said flowing fluid and said fluid batch sample on a time sharing basis.

9. The spectrometer of claim 1 wherein:
said analyzer is a multi channel analyzer for analyzing flowing fluid excitation response to signals received from said processor and which are derived from said first detector, and separately analyzing batch sample fluid excitation response signals received from said processor and which are derived from said second detector, whereby simultaneous analysis of flowing fluid in said first passageway and of fluid in a batch sample arc enabled.

10. The spectrometer of claim 1 wherein:
the flowing fluid is a lubricating oil flowing through an operating engine; and the batch sample fluid is fuel for said engine.

11. An x-ray fluorescence spectrometer for on-site determination of some components in a flowing fluid target and in a stationary sample target of a different fluid comprising:
an x-ray fluorescence source block having a flowing fluid target in one location and a stationary sample fluid target in another separate location, said block containing first and second different radionuclide sources, the first source being situated in the block to direct radiation oriented in a different direction from the direction of radiation from the second source to enable the first source to excite the flowing fluid target and enable the second source to excite the stationary sample fluid target;

two separate detectors arranged to detect fluorescent x-rays from the said flowing fluid target separately from said stationary sample fluid target;

a signal processor coupled to said detectors for separate processing of signals from said detectors; and a signal analyzer coupled to said processor for analyzing output signals from said processor to identify components in said fluids represented by the outputs from said detectors.

12. The spectrometer of claim 11 wherein:

said sources are located between said targets on a line intercepting said targets, with each source oriented to direct radiation in a direction within about 30 degrees of 180 degrees from the direction of radiation from the other source.

13. The spectrometer of claim 12 wherein:

said flowing fluid is lubricating oil and said stationary sample fluid is fuel oil;

said components to be determined are contaminants;

said spectrometer further comprising:

a passageway for said lubricating oil in said source block and exposed to said first source; and a receiver for said stationary sample of fuel oil and exposed to said second source.

14. The spectrometer of claim 13 further comprising:

a computer coupled to said analyzer to process signals from said analyzer; and a user interface coupled to said computer to produce human readable information derived from analysis of said oils and representing certain chemicals contained in said oils.

15. The spectrometer of claim 14 wherein:

said first source is cadmium 109 and said second source is iron 55.

16. The spectrometer of claim 14 wherein:

said computer has an input coupled to said analyzer to receive signals from said first detector and said second detector; and said computer has an output coupled to said signal processor to schedule sampling, processing and analyzing events on a time-sharing basis for control of said analyzer to share time between analysis of signals from the processor for said first detector and analysis of signals from the processor for said second detector.

17. The spectrometer of claim 14 wherein:

said analyzer is a multi channel analyzer for simultaneous analysis of flowing oil sample and batch sample oil.

18. The spectrometer of claim 14 further comprising:

a door normally covering said receiver and inhibiting passage of radiation from said receiver outside the spectrometer, said door being manually operable to an open position; and a sample vial of material of low molecular weight and holding a sample of a batch sample oil and enabling entry of radiation from said second source and exit of radiation from excited batch sample oil in said vial to said second detector when said door has been opened to admit said vial to said receiver and said vial is located in said receiver and exposed to radiation from said second source.

19. A method of analyzing fluids in batch samples and flowing fluids in a single instrument comprising:

providing at least two sources of X-ray radiation in a single source block;

flowing a first fluid through said source block and exposing said flowing fluid to radiation from one of said sources;

placing a sample of a second fluid in said source block and exposing said sample to radiation from said second source;

detecting radiation from flowing fluid exposed to radiation from said first source and producing an output signal representative of the radiation from said flowing fluid;

detecting radiation from the fluid sample exposed to said second source and producing an output signal representative of the radiation from said fluid sample;

coupling said signals to an analyzer; and separately analyzing signals from said flowing fluid and signals from said fluid sample.

20. The method of claim 19 further comprising:

while analyzing signals from said flowing fluid, producing output signals representing certain chemical elements present in said flowing fluid; and while analyzing signals from said fluid sample, producing output signals representing certain chemical elements in said fluid sample.

21. The method of claim 20 further comprising:

coupling said output signals to a machine health monitoring system.

22. The method of claim 20 further comprising:

shielding said flowing fluid from radiation from said second source; and shielding said fluid sample from radiation from said first source.

23. The method of claim 22 further comprising:

using a second fluid of different composition from said first fluid.

24. The method of claim 23 further comprising two different isotopes for said sources.

25. In a system including a flowing fluid and storage for a separate fluid, apparatus for sampling and analyzing said flowing fluid and for sampling and analyzing said separate fluid comprising:

the x-ray fluorescence spectrometer of claim 1;

a flowing fluid and a pump moving said flowing fluid through said first passageway of the sampler body;

a container storing said separate fluid; and a batch sample of said separate fluid from said storage container and disposed in said batch sample receiver in said body.

26. The apparatus of claim 25 wherein:

said flowing fluid is engine lubricating oil; and said separate fluid is engine fuel oil.

27. The apparatus of claim 26 wherein:

the system is a boat and further comprises:

an engine having a lubricating oil circulating system coupled to said first passageway of the sampling body and delivering said lubricating oil through said body;

a container storing said fuel and coupled to said engine to supply fuel to said engine; and said batch sample is fuel oil taken from said container and disposed in said receiver in said body.

28. The apparatus of claim 27 further comprising:
an engine controller coupled to said computer output and responsive to signals from said computer to change engine operation.

29. The apparatus of claim 28 and further comprising:
an annunciator coupled to said computer and responsive to results of analysis by said analyzer to alert a user.

30. A dual source x-ray fluorescence spectrometer comprising:
an x-ray fluorescence source block having first and second fluid targets in separate locations in said source block and having a plurality of passageways therein,
first and second different radionuclide sources positioned in said source block to direct radiation in different directions through the passageways in said source block wherein said first source is positioned to excite said first fluid target and said second source is positioned to excite said second fluid target;
first and second detectors arranged to detect fluorescent x-rays emitted by said first and second fluid targets respectively, wherein said detectors are positioned in said source block such that they are not in direct line of sight with said radionuclide sauces and are substantially shielded from radiation from said radionuclide sources by said source block;
a signal processor coupled to said detectors for separate processing of signals from said detectors; and
a signal analyzer coupled to said processor for analyzing output signals from said processor to identify components in said fluids represented by the outputs from said detectors.

31. The spectrometer of claim 30 and wherein:
said sources are located generally between said targets, with said first source directing radiation toward said first target in a direction between 150 and 210 degrees of the direction said second source directs radiation toward said second target.

32. The spectrometer of claim 30 and further comprising:
a computer coupled to said analyzer to process signals from said analyzer; and
a user interface coupled to said computer to produce human readable information derived from analysis of said fluid targets and representing certain chemicals contained in said fluid targets.

33. The spectrometer of claim 32 wherein:
said computer has an input coupled to said analyzer to receive signals from said first detector and said second detector; and
said computer has an output coupled to said signal processor to schedule sampling, processing and analyzing events on a time-sharing basis for control of said analyzer to share time between analysis of signals from the processor for said first detector and analysis of signals from the processor for said second detector.

34. The spectrometer of claim 33 wherein:
said analyzer is a multi channel analyzer for simultaneous analysis of flowing oil sample and batch sample oil.

35. The spectrometer of claim 33 and wherein:
at least one of said fluid targets is a flowing fluid.

36. The spectrometer of claim 33 wherein at least one of said fluid targets is a batch sample, said spectrometer further comprising a door on said housing being selectively operable to either cover or permit access to a well for receiving a batch sample vial.

37. The spectrometer of claim 30 wherein said source block defines a first noise reduction chamber positioned on a line between said first source and said first fluid target and a second noise reduction chamber positioned on a line between said second source and said second fluid target, said first and second noise reduction chambers operable to receive radiation directed from said first and second sources through the passageways and through said first and second fluid targets respectively.

38. The spectrometer of claim 37 wherein said noise reduction chambers have a size dimension relative to the line between the respective source and fluid target that is substantially greater than the size dimension of the passageway between the respective source and fluid target.

39. A dual source x-ray fluorescence spectrometer comprising:
an x-ray fluorescence source block having first and second fluid targets in separate locations in said source block and having a plurality of passageways therein,
first and second x-ray sources positioned in said source block to direct radiation in different directions through the passageways in said source block wherein said first source is operable to excite said first fluid target and said second source is operable to excite said second fluid target;
first and second detectors arranged to detect fluorescent x-rays emitted by said first and second fluid targets,
wherein said source block defines a first noise reduction chamber positioned along a first centerline of a passageway between said first fluid target and said first x-ray source with said first fluid target between said first noise reduction chamber and said first x-ray source such that x-rays from said first source that pass through said first fluid target can be received by said first noise reduction chamber,
wherein said first detector is positioned in the source block such that it does not intersect the centerline of the passageway between said first detector and said first fluid target,
a signal processor coupled to said detectors for separate processing of signals from said detectors; and
a signal analyzer coupled to said processor for analyzing output signals from said processor to identify components in said fluids represented by the outputs from said detectors.

40. The spectrometer of claim 39 wherein said source block includes first and second portions of substantially different material composition.

41. The spectrometer of claim 39 wherein said source block defines a second noise reduction chamber positioned along a second centerline of a passageway between said second fluid target and said second x-ray source with said second fluid target between said second noise reduction chamber and said second x-ray source such that x-rays from said second source that pass through said second fluid target can be received by said second noise reduction chamber.

42. The spectrometer of claim 41 wherein the first and second centerlines are substantially parallel.

43. The spectrometer of claim 39 wherein said first fluid target is contained in a flow path defined by a tube substantially transparent to x-rays from said first x-ray source.

44. The spectrometer of claim 43 wherein said second fluid target is a batch fluid sample.

* * * * *